United States Patent
Kwak et al.

(10) Patent No.: US 11,952,687 B2
(45) Date of Patent: *Apr. 9, 2024

(54) METHOD FOR PRODUCING CELL-CULTURING POLYVINYL ALCOHOL NANOFIBER STRUCTURE

(71) Applicant: NANOFAENTECH CO., LTD., Gimhae-si (KR)

(72) Inventors: Jong Young Kwak, Suwon-si (KR); Jung Min Kim, Suwon-si (KR); Yeo Jin Park, Bucheon-si (KR); Dan Bi Park, Seongnam-si (KR); Qasaim Muhammad, Suwon-si (KR); Young Hun Jeong, Daegu (KR)

(73) Assignee: NANOFAENTECH CO., LTD., Gimhae-si (KR)

( * ) Notice: Subject to any disclaimer, the term of this patent is extended or adjusted under 35 U.S.C. 154(b) by 1484 days.

This patent is subject to a terminal disclaimer.

(21) Appl. No.: 16/319,148

(22) PCT Filed: Jan. 12, 2017

(86) PCT No.: PCT/KR2017/000393
§ 371 (c)(1),
(2) Date: Jan. 18, 2019

(87) PCT Pub. No.: WO2018/016701
PCT Pub. Date: Jan. 25, 2018

(65) Prior Publication Data
US 2021/0332511 A1  Oct. 28, 2021

(30) Foreign Application Priority Data
Jul. 19, 2016  (KR) .................. 10-2016-0091502

(51) Int. Cl.
*D04H 1/4309* (2012.01)
*C12N 5/00* (2006.01)
(Continued)

(52) U.S. Cl.
CPC ......... *D04H 1/4309* (2013.01); *C12N 5/0068* (2013.01); *D01D 5/003* (2013.01);
(Continued)

(58) Field of Classification Search
CPC .... D04H 1/4309; D04H 1/728; C12N 5/0068; C12N 2533/30; C12N 2537/10;
(Continued)

(56) References Cited

U.S. PATENT DOCUMENTS 11,643,634 B2 *  5/2023  Kwak .................. D01F 6/34
                                                           435/401
2012/0107900 A1  5/2012  Greiner et al.

FOREIGN PATENT DOCUMENTS

KR  10-1992-0019926 A  11/1992
KR  10-2007-0099926 A  10/2007
(Continued)

OTHER PUBLICATIONS

International Search Report for PCT/KR2017/000393 dated Apr. 19, 2017 (PCT/ISA/210).

*Primary Examiner* — Jeffrey M Wollschlager
(74) *Attorney, Agent, or Firm* — Sughrue Mion, PLLC

(57) ABSTRACT

The present disclosure provides a method for producing a cell-culturing polyvinyl alcohol-based nanofiber structure, the method comprising: electrospinning an electrospun solution to form a nanofiber mat, wherein the electrospun solution contains polyvinyl alcohol (PVA), polyacrylic acid (PA) and glutaraldehyde (GA); crosslinking the nanofiber mat via a hydrochloric acid (HCl) vapor treatment; and
(Continued)

treating the crosslinked nanofiber mat with dimethylformamide (DMF) solvent to crystallize the nanofiber mat.

6 Claims, 10 Drawing Sheets

(51) Int. Cl.
    *D01D 5/00*    (2006.01)
    *D01D 10/02*    (2006.01)
    *D01D 10/06*    (2006.01)
    *D04H 1/728*    (2012.01)
    *D06M 11/11*    (2006.01)
    *D06M 13/127*    (2006.01)
    *D06M 13/402*    (2006.01)

(52) U.S. Cl.
    CPC ......... *D01D 5/0038* (2013.01); *D01D 5/0069* (2013.01); *D01D 10/02* (2013.01); *D01D 10/06* (2013.01); *D04H 1/728* (2013.01); *D06M 11/11* (2013.01); *D06M 13/127* (2013.01); *D06M 13/402* (2013.01); *C12N 2533/30* (2013.01)

(58) Field of Classification Search
    CPC .... D01D 5/003; D01D 5/0038; D01D 5/0069; D01D 10/02; D01D 10/06; D01D 5/00; D01D 1/02; D06M 11/11; D06M 13/127; D06M 13/402; D06M 2101/24; D06M 2101/26; D06M 7/00; D01F 1/10; D01F 6/50; D10B 2509/00
    See application file for complete search history.

(56) References Cited

FOREIGN PATENT DOCUMENTS

| KR | 20110018114 | * | 2/2011 |
| KR | 10-2011-0028019 A | | 3/2011 |
| KR | 10-2014-0091448 A | | 7/2014 |

* cited by examiner

[FIG. 1]
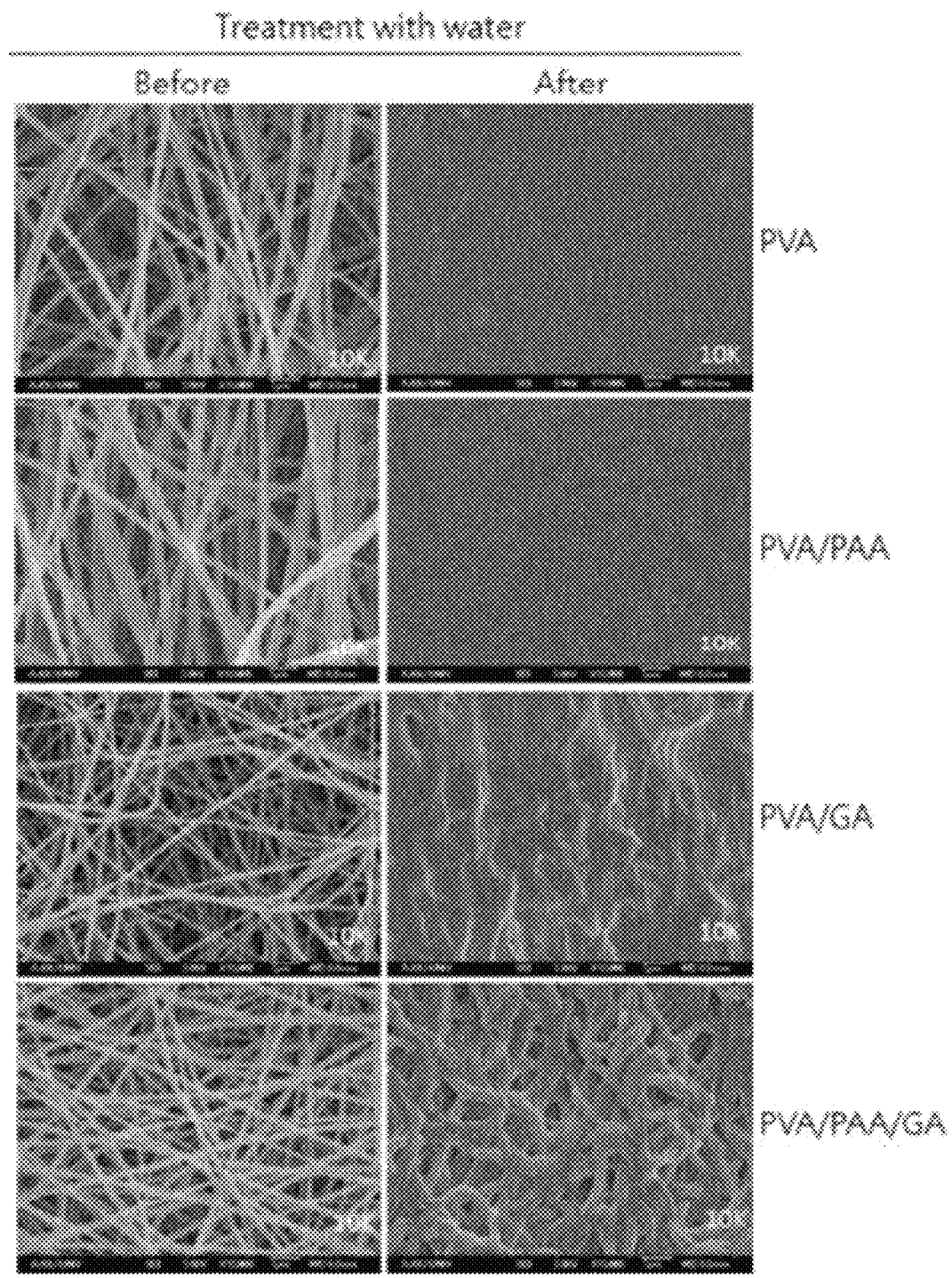

[FIG. 2]
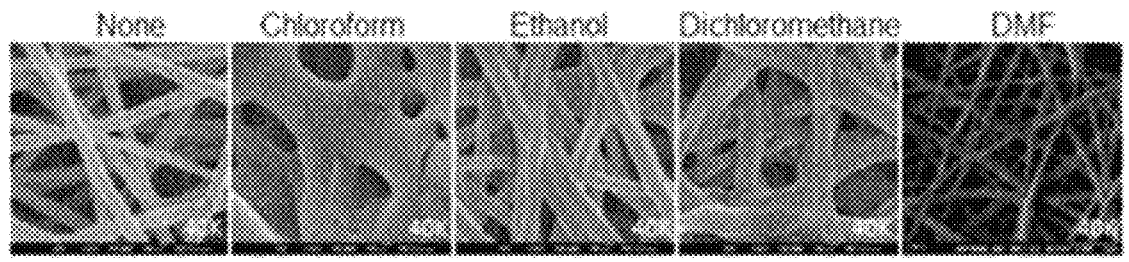
[FIG. 3]
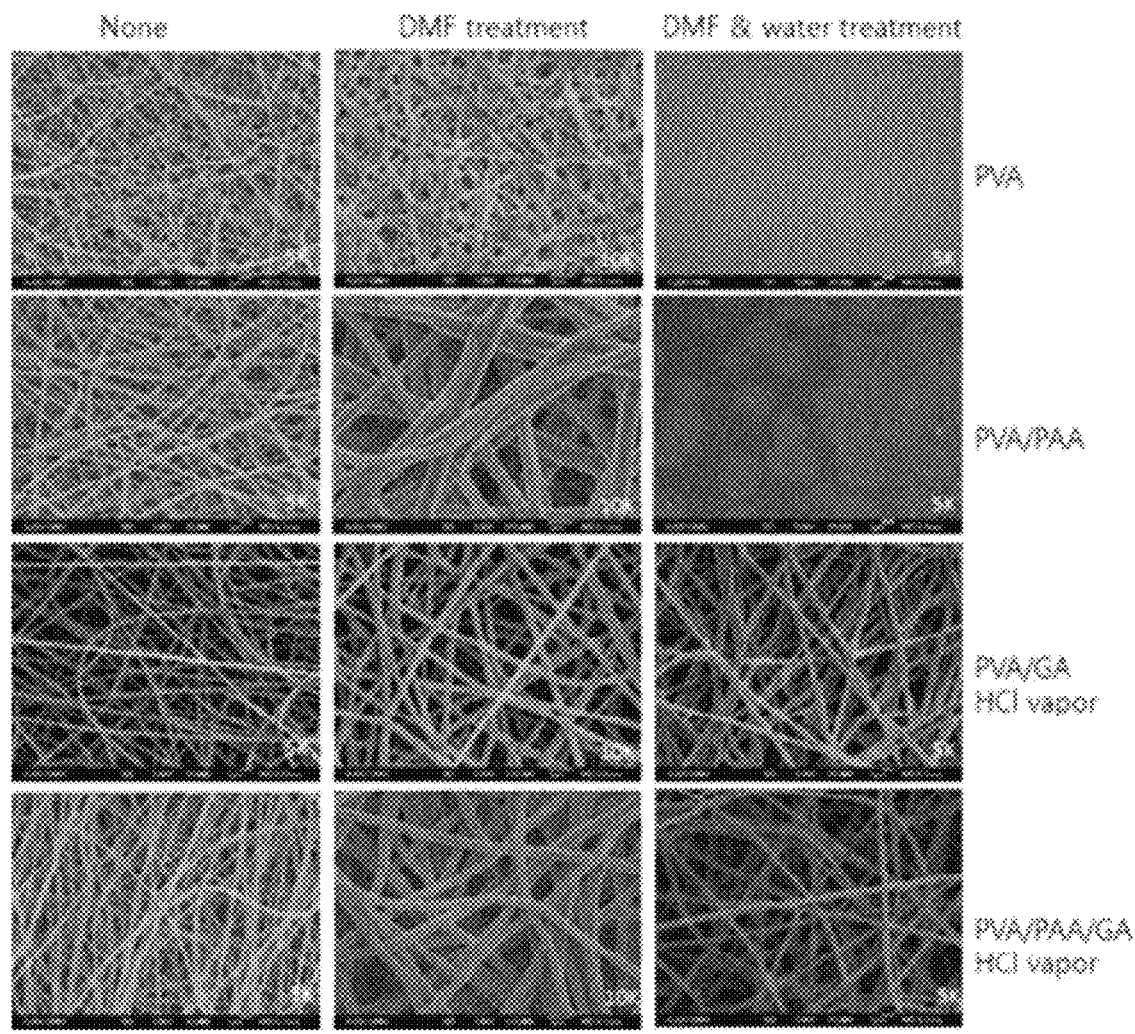

[FIG. 4]
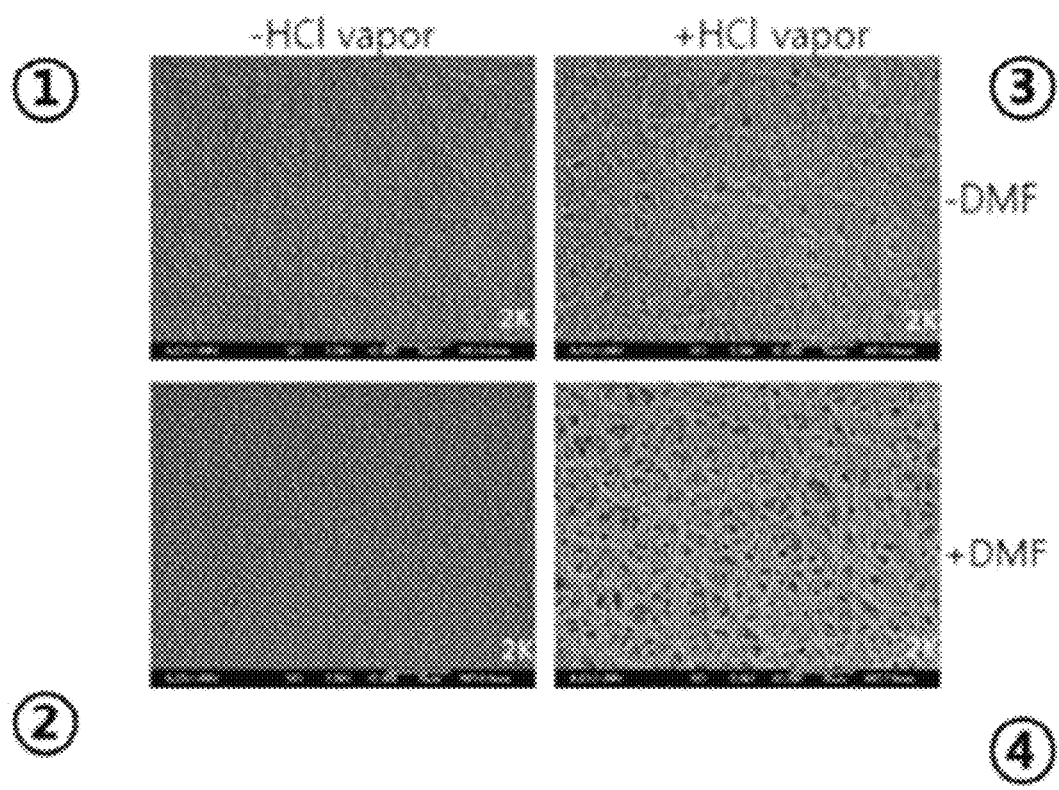

[FIG. 5]
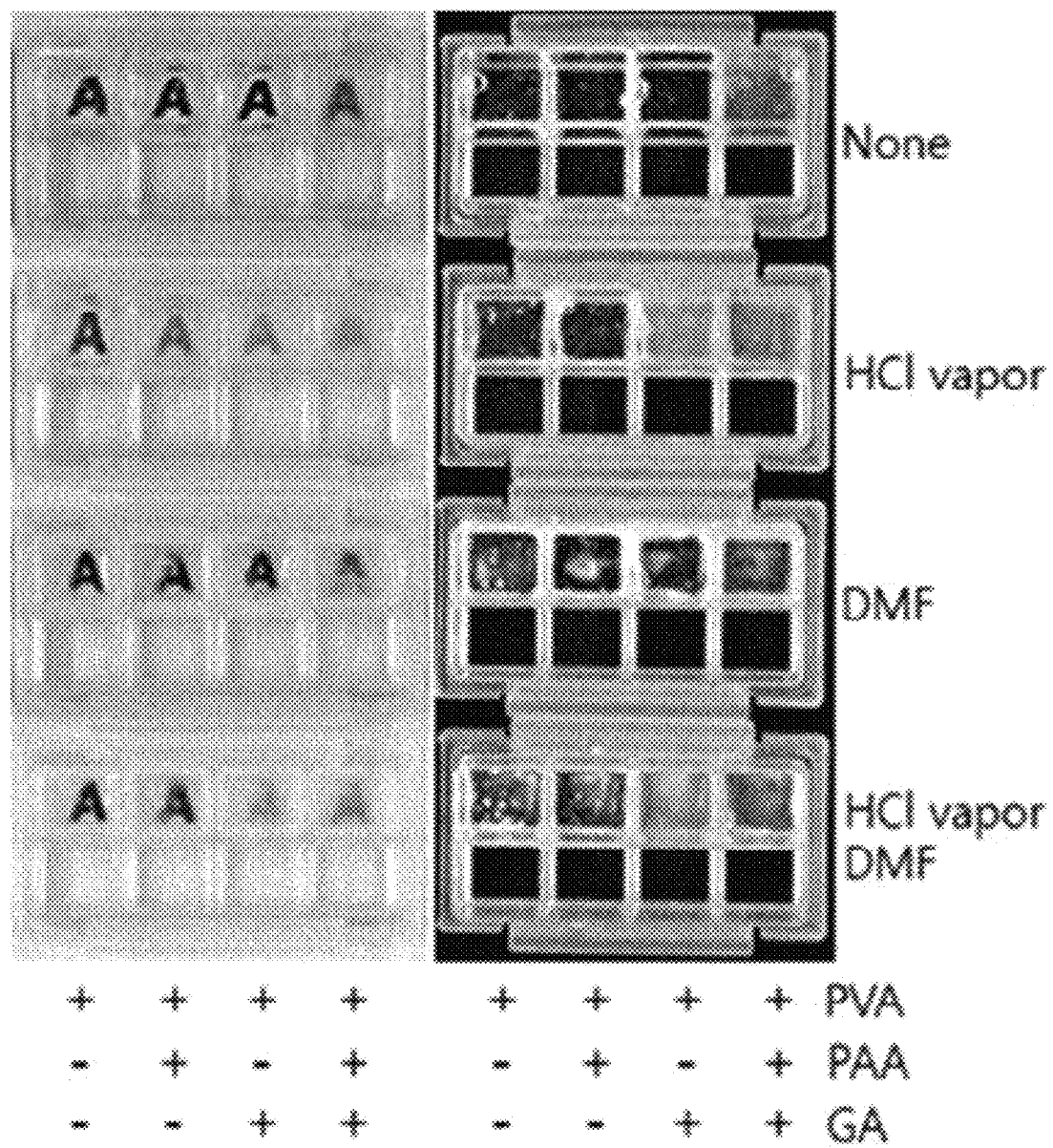

[FIG. 6]
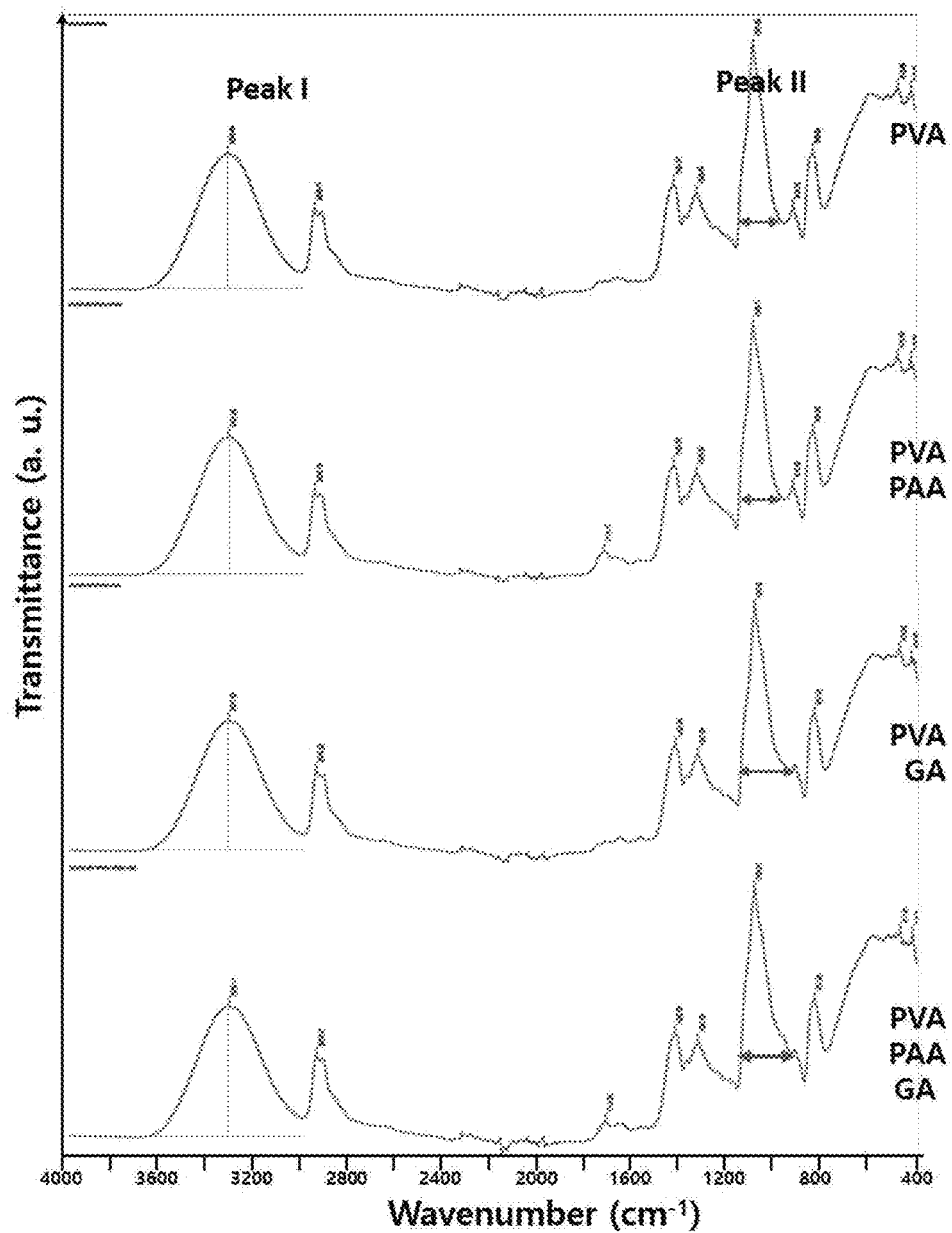

[FIG. 7]
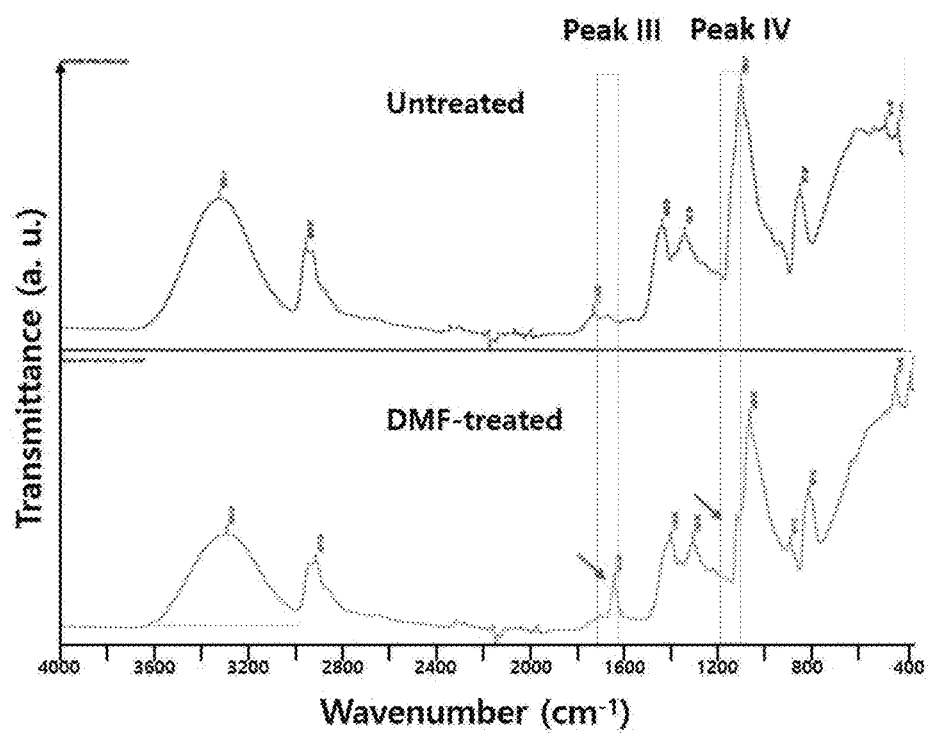

[FIG. 8]
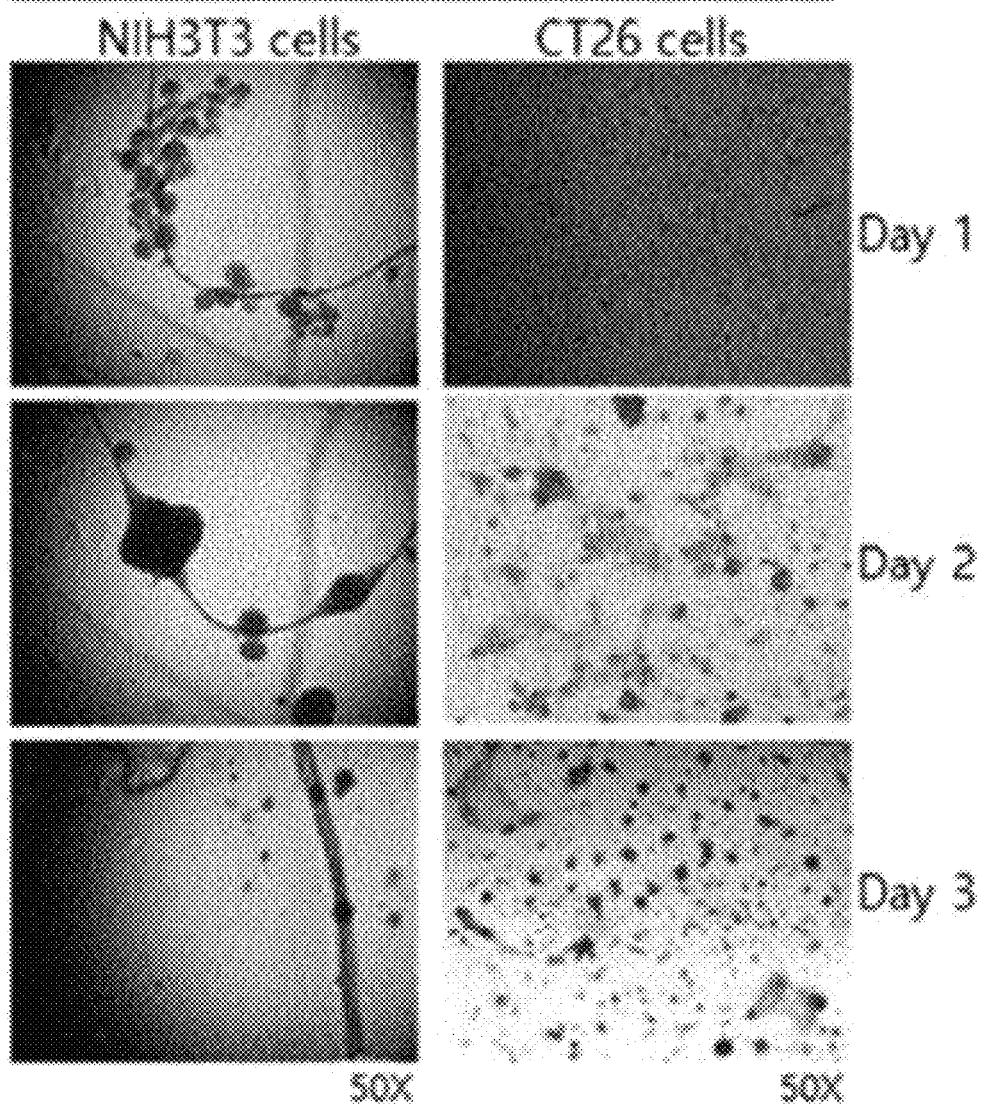

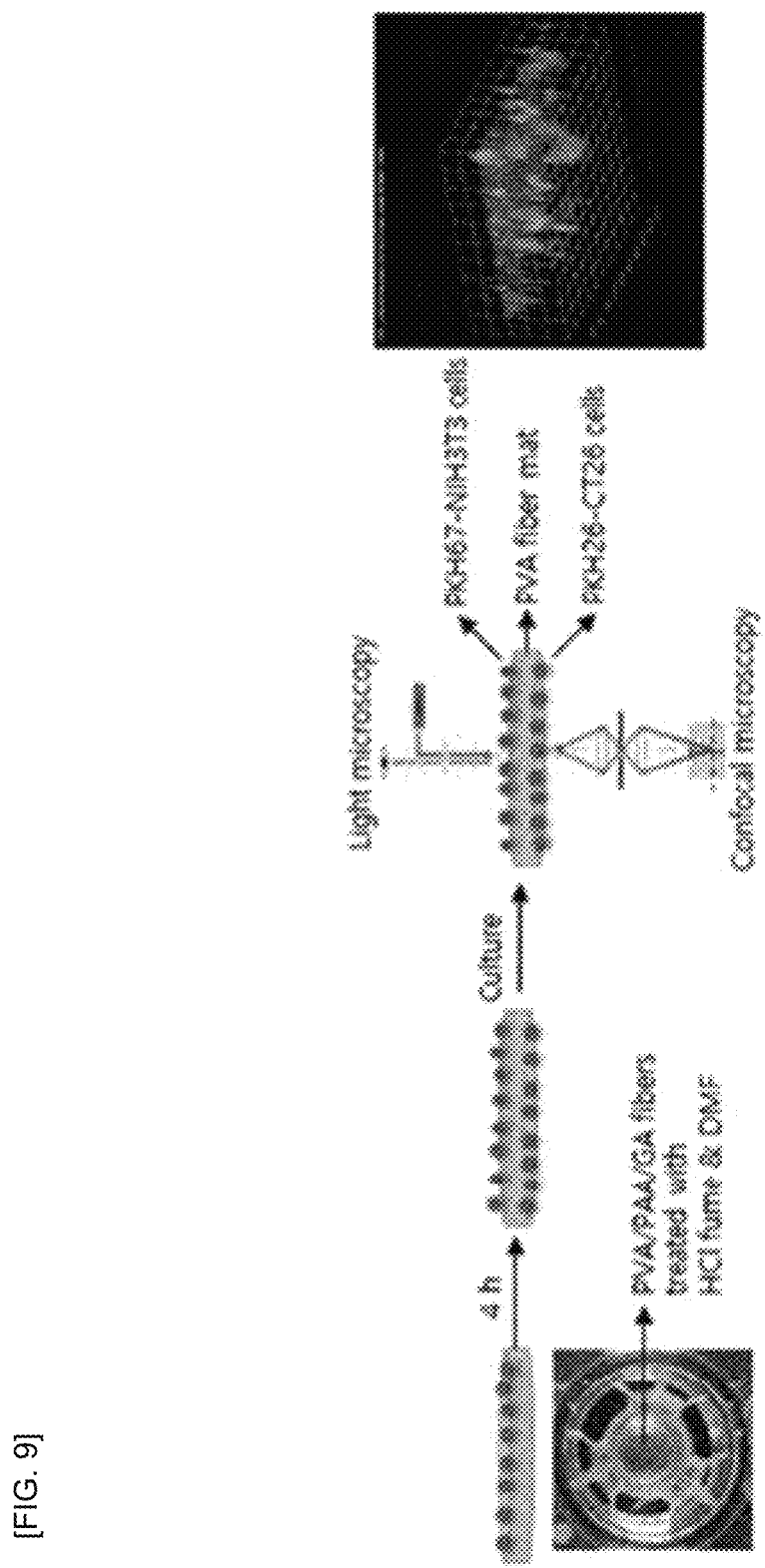
[FIG. 9]

[FIG. 10]
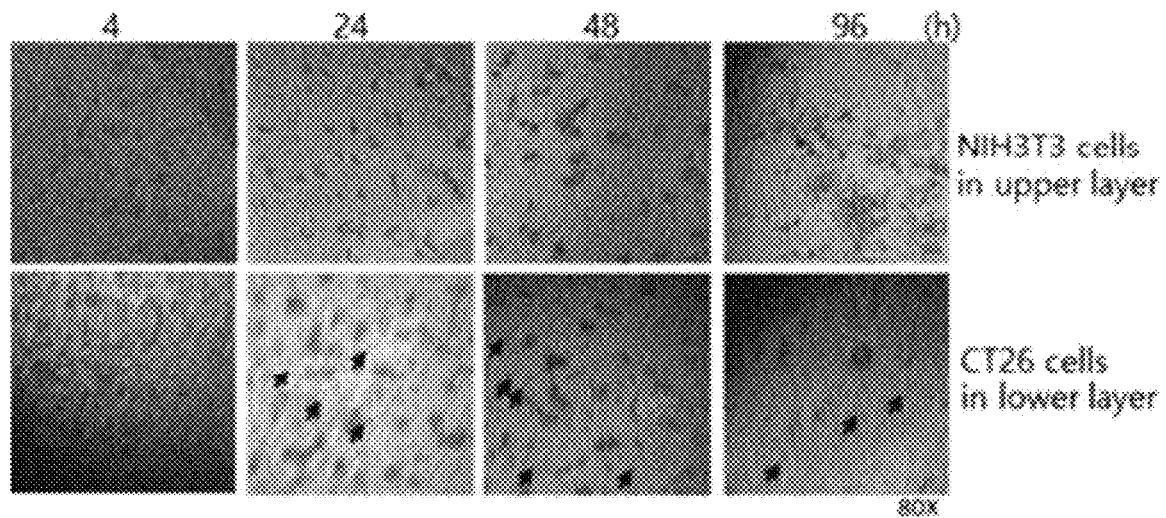
[FIG. 11]
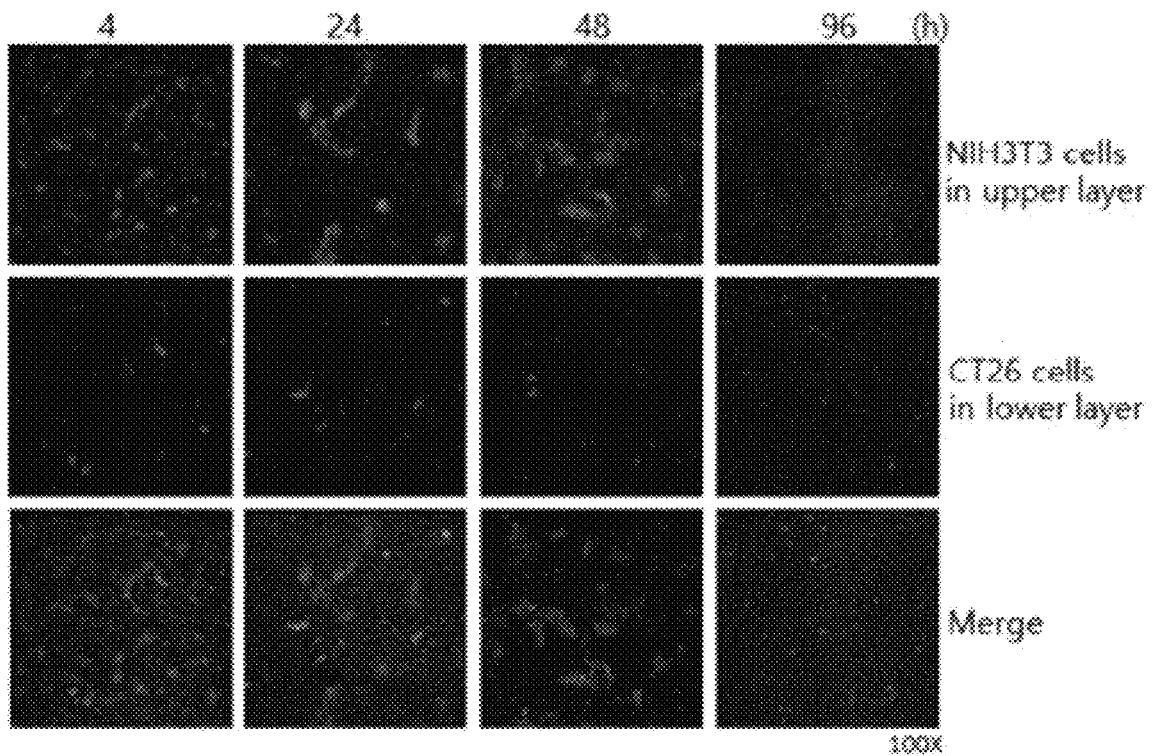

[FIG. 12]
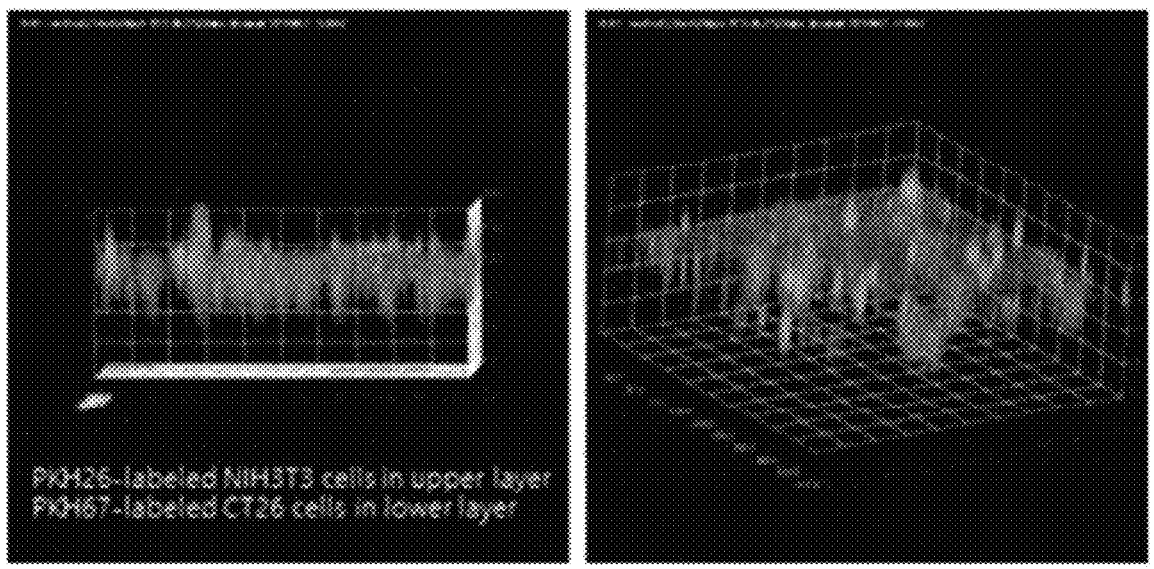
[FIG. 13]
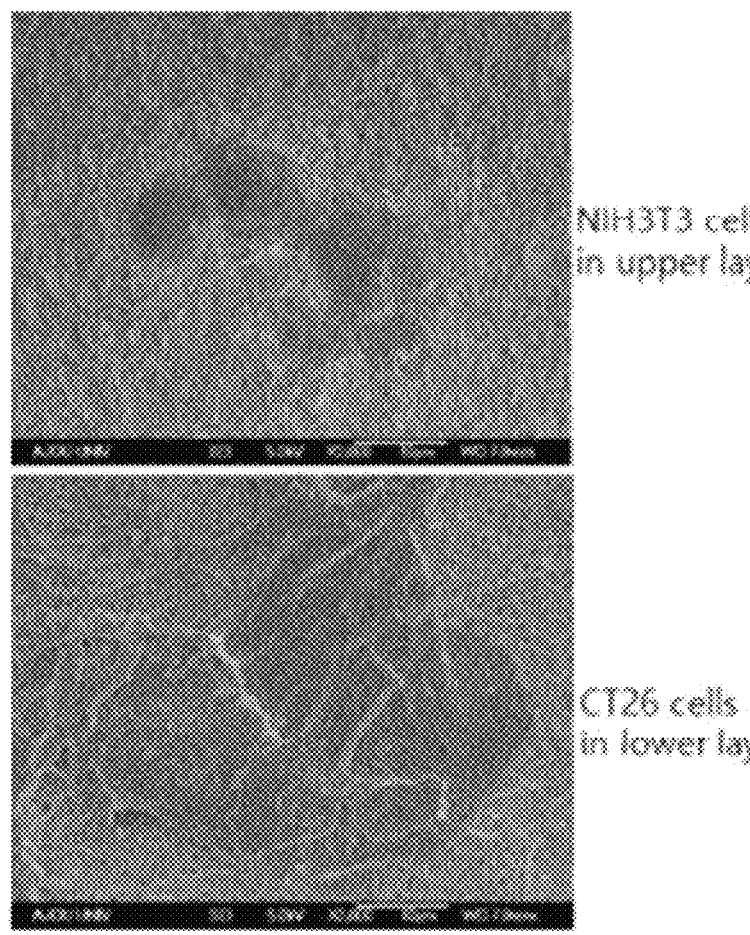

METHOD FOR PRODUCING CELL-CULTURING POLYVINYL ALCOHOL NANOFIBER STRUCTURE

CROSS REFERENCE TO RELATED APPLICATIONS

This application is a National Stage of International Application No. PCT/KR2017/000393 filed Jan. 12, 2017, claiming priority based on Japanese Patent Application No. 10-2016-0091502 filed Jul. 19, 2016.

1. Field

The present disclosure relates to a method for producing a cell-culturing polyvinyl alcohol nanofiber structure. More particularly, the present disclosure relates to a method for producing a cell-culturing polyvinyl alcohol nanofiber structure capable of enhancing water-resistance while ensuring certain transparency.

2. Description of Related Art

Although polyvinyl alcohol (PVA) has the advantages of high hydrophilicity, permeability, biocompatibility and biodegradability, the PVA has a high solubility in water and has therefore a limitation for being used as a material for cell culture. When producing nanofibers using the PVA, and when the degree of saponification indicating the degree of hydrolysis of the PVA is 99.8% or smaller, an acetate group present in the PVA prevents hydrogen bonding between the polymer chains. As a result, the water can easily penetrate into the corresponding portion, thereby deteriorating the water resistance of the PVA fiber.

Generally, the degree of saponification of commercially available PVA is typically smaller than 99.8%. When the nanofiber was prepared using the commercially available PVA, the nanofiber easily dissolves in water. To increase the water-resistance of nanofiber made of the PVA, the crosslinking of the PVA is also carried out. Representative methods of the crosslinking include a physical crosslinking method using heat treatment or crystallization and a chemical crosslinking method using a crosslinking agent (See Korean Patents No. 10-0703607, No. 10-0841463, No. 10-0835082). However, unlike the non-crosslinked PVA, the crosslinked PVA is reduced in an optical transmittance due to the changing of its crystallinity.

In addition to the crosslinking method, another method for improving the water-resistance of PVA nanofiber is disclosed in Korean Patent No. 10-1413095. In this work, a PVA aqueous solution and glyoxal are added to the aqueous solution. In this connection, the aqueous solution employs a natural protein water-soluble solution and/or a low-molecular-weight chitosan aqueous solution. The water-soluble solution may be electro-spun to produce a water-insoluble and transparent nanofiber membrane.

Further, polyacrylic acid (PAA) contains carboxyl groups structurally. Thus, combining the PAA with the hydroxyl group of the PVA allows the PVA to have a crosslinked structure. Accordingly, the solubility of the resulting PVA in an aqueous solution can be lowered. Destaye et al. (ACS Appl. Mater Interfaces, Vol. 5, 4745-4752, 2103) has reported that the cross-linking is achieved by the intermolecular acetal linkage between the aldehyde group of the glutaraldehyde (GA) and the hydroxyl group of the PVA. The crosslinking reduces the number of the hydroxyl groups in the PVA and thus the PVA has a low solubility in aqueous solution.

Meanwhile, when the crystallinity of PVA is 0 or 1, the PVA has optical transparency. When the PVA has the crystallinity value of between 0 exclusive and 1 exclusive by the crosslinking of the PVA, the transparency of PVA is lowered by light scattering. In other words, water-resistance may be improved via the crosslinking of PVA, which may cause the transparency of the PVA to be lowered. When the nanofiber made from such optically non-transparent PVA is used as a cell-culturing mat, there is a disadvantage that the user cannot easily observe the cell culturing in the mat.

For this reason, in the biotechnology field, there is a need for a technique for manufacturing a PVA nanofiber mat, which may improve the water resistance of the mat while maintaining the transparency of the mat itself.

DISCLOSURE

Technical Purposes

A purpose of the present disclosure is to provide a method for producing a cell-culturing PVA nanofiber structure with the transparency and the improved water resistance.

Technical Solutions

In one aspect, there provided a method for producing a cell-culturing PVA-based nanofiber structure, the method comprising: electrospinning an electrospun solution to form a nanofiber mat, wherein the electrospun solution contains polyvinyl alcohol (PVA), polyacrylic acid (PA) and glutaraldehyde (GA); crosslinking the nanofiber mat via a hydrochloric acid (HCl) vapor treatment; and treating the crosslinked nanofiber mat with dimethylformamide (DMF) solvent to crystallize the nanofiber mat.

In one embodiment, forming the nanofiber mat includes: electrospinning the electrospun solution at a spinning rate of 5 to 10 µl/min using a metal syringe at 10 to 15 kV to form nanofibers; and performing a thermal treatment of the nanofibers.

In one embodiment, crosslinking the nanofiber mat includes: adding the nanofiber mat and HCl into a vacuum desiccator and treating the nanofiber mat with the HCl vapor under vacuum for 60 to 120 seconds.

In one embodiment, crystallizing the nanofiber mat includes: treating the crosslinked nanofiber mat with the DMF solvent for 20 seconds to 1 minute; and drying the nanofiber mat.

In one embodiment, the crystallized nanofiber mat via the crystallizing is not gelated when the crystallized nanofiber mat is treated with distilled water.

In one embodiment, the method further comprises: after the crystallization, adhering two or more different kinds of cells on both faces of the crystallized nanofiber mat respectively, culturing the cells, and observing the cells on the both faces at the same time.

Technical Effects

According to the method for producing the cell-culturing PVA nanofiber structure in accordance with the present disclosure as described above, the nanofiber structure with the improved water-resistance and the ensured transparency to an extent allowing the cell culturing condition to be visually observed may be produced. In particular, the nanofiber structure as produced by the present method has the advantage of allowing the different kinds of cells to be attached on both faces thereof respectively and allowing the user to check the cultured state of the cells in real time using a microscope.

BRIEF DESCRIPTION OF THE DRAWINGS

FIG. 1 shows scanning electron microscope (SEM) images to illustrate a water-resistance of a nanofiber mat immediately after an electrospinning process for each electrospun solution.

FIG. 2 shows SEM images of the nanofiber structure of the nanofiber mat after a solvent treatment process for each solvent type.

FIG. 3 shows SEM images of the nanofiber structure after treating distilled water for the nanofiber mat prepared according to Present Example 1, Comparative Examples 1-a, 1-b and 2.

FIG. 4 shows experimental results to illustrate effects by a HCl vapor treatment process and a DMF treatment process.

FIG. 5 shows photographs for illustrating results of transparency evaluation for each nanofiber mat.

FIG. 6 shows an infrared spectroscopic finding of the nanofiber mats before the DMF solvent treatment process thereof.

FIG. 7 shows the infrared spectroscopic finding of a PVA/PAA/GA nanofiber mat before and after the DMF solvent treatment process thereof.

FIG. 8 shows photographs for illustrating results of cell adhesion evaluation to a nanofiber mat prepared according to Comparative Example 2.

FIG. 9 is a diagram illustrating a process for fabricating a cell-culturing nanofiber mat using a nanofiber mat manufactured according to Present Example 1 of the present disclosure.

FIGS. 10 to 13 show photographs for illustrating results of cell adhesion evaluation to the nanofiber mat prepared according to the process of FIG. 9.

DETAILED DESCRIPTIONS

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Method for Producing Nanofiber Mat

The method for producing the nanofiber mat according to the present disclosure may include, first, electrospinning an electrospun solution containing polyvinyl alcohol (PVA), polyacrylic acid (PAA) and glutaraldehyde (GA) to form a nanofiber mat.

The electrospun solution includes PVA, GA, and a distilled water as a solvent.

In the electrospinning process, the electrospun solution may be electro-spun using a metal syringe at a spinning rate of 5 to 10 μl/min to form the nanofiber. In this connection, a voltage condition for the electrospinning process may be 10 to 15 kV. When the electrospun solution is performed at the spinning speed and voltage condition, the stably structural nanofiber with a constant diameter and with no bead formation may be formed. In this connection, the nanofiber mat may be formed by integrating the nanofibers formed via the electrospinning process. The integration of the nanofibers and the electrospinning process may be performed simultaneously by using a drum integrating plate in the electrospinning process. The electrospinning process involves performing thermal treatment on the nanofiber.

The PVA/PAA/GA nanofiber mat may be manufactured via the electrospinning process as described above.

Then, the nanofiber mat was treated with HCl vapor such that the nanofiber is crosslinked. The nanofiber mat as treated with the HCl vapor is then crystallized by a solvent treatment using DMF to produce a cell-culturing PVA nanofiber structure.

The HCl vapor treatment may be carried out by adding the nanofiber mat and HCl into a vacuum desiccator and treating the nanofiber mat with the HCl vapor under a vacuum for 60 to 120 seconds. The PVA and PAA of the nanofiber mat may be crosslinked by HCl vapor treatment.

The crystallization process may be performed by the DMF solvent treatment followed by drying. The DMF solvent treatment may be performed for 20 seconds to 1 minute. The water-resistance can be improved by crystallizing the PVA via the DMF solvent treatment. Accordingly, after the crystallization step, the crystallized nanofiber mat is not gelated even when treated with distilled water, and at the same time, the optical transparency of the PVA and the PAA themselves is maintained.

After the crystallization step, cells may be cultured by attaching two or more different cells to the both faces of the crystallized nanofiber mat respectively. The PVA/PAA/GA nanofiber mat according to the present disclosure may be easily used for cell-culturing because the cells may be easily attached to the mat even when the DMF solvent treatment is performed. The PVA/GA nanofiber mat may have very lower cell adhesion and thus may not be used for cell-culturing.

Hereinafter, the present disclosure will be more specifically illustrated by way of concrete Present Examples and Experiments.

Present Example 1

Electrospun solution was prepared by mixing polyvinyl alcohol (PVA, Mw=89,000 to 98,000 99+% hydrolyzed, Sigma), polyacrylic acid (PAA, Mw=2000, Sigma) and distilled water as a solvent. In this connection, the PVA was mixed at 10% (w/v) relative to the distilled water. The PAA was mixed at 0.2% (w/v) relative to the distilled water. They were mixed and dissolved at 80° C. for 2 to 3 hours. After cooling the completely dissolved PVA solution at a room temperature, glutaraldehyde (GA) was added at 2% (V/V) thereto to form a final mixture which in turn was held for 24 hours. In this manner, the electrospun solution (PVA/PAA/GA solution) was obtained.

The electrospun solution (PVA/PAA/GA solution) as prepared above was used to prepare a nanofiber mat. 2 mL of the electrospun solution (PVA/PAA/GA solution) was electro-spun at 10 kV using a 27G metal syringe at a spinning rate of 8 μl/min at a spinning distance of 10 cm. The nanofiber prepared by the electrospinning was heat-treated at 60° C. for 40 seconds. The thickness of PVA nanofiber mats was 50±7 μm.

In order to crosslink the heat treated nanofiber, the nanofiber and HCl were added to a vacuum desiccator for catalytic reaction for the crosslinking. Then, the nanofiber was treated with the HCl vapor under vacuum for 60 to 120 seconds. Then, the HCl vapor treated nanofiber was treated with DMF solution for 30 seconds and then dried.

Comparative Example 1-a

Except for using PVA/GA solution as an electrospun solution in this comparative example, the electrospinning process, the HCl vapor treatment process, and the solvent treatment process were performed in substantially the same manner as in the method for preparing the nanofiber mat according to Present Example 1. Thus, the nanofiber mat was prepared according to Comparative Example 1-a. In this connection, the PVA/GA solution was obtained by dissolving the PVA and GA in the distilled water at a room temperature. The GA content was 2% (V/V) based on the content of the distilled water.

Comparative Examples 1-b and 2

PVA solution and PVA/PAA solution were respectively prepared as electrospun solutions for preparing nanofiber mats according to Comparative Examples 1-b and 2. In this connection, the PVA solution was prepared by mixing PVA with distilled water at 10% (w/v) thereof relative to the distilled water. Then, the mixed solution was stirred at 80° C. for 2 to 3 hours. Thus, the PVA solution was prepared. Further, The PVA/PAA solution was obtained as follows: PVA was added to distilled water at 10% (w/v) thereof relative to the distilled water. The mixed solution thus obtained was mixed with PAA at 0.2% (w/v) thereof relative to the distilled water. Then, the mixed solution was stirred at 80° C. for 2 to 3 hours.

Each of the PVA solution and the PVA/PAA solution was subjected to the electrospinning process and the DMF solvent treatment process in the method for manufacturing the nanofiber mat according to the Present Example 1. Thus, nanofiber mats according to Comparative Example 1-b and Comparative Example 2 were prepared.

Experiment 1: Water-Resistance Evaluation of Nanofiber Mat Immediately after Electrospinning Process The HCl vapor treatment process and solvent treatment process were omitted from the process of manufacturing the nanofiber mat according to Present Example 1, Comparative Examples 1-a, 1-b and 2 as exemplified above. That is, the nanofiber mats immediately after the electrospinning process were prepared. Nanofiber mat images were taken from the nanofiber mats immediately after the electrospinning process, using SEM. Next, each nanofiber mat was treated with distilled water, and then each nanofiber mat image was taken therefrom using a SEM. The results are shown in FIG. 1.

For observation using the electron microscope, the nanofiber was coated with platinum and then observed via the SEM using JSM-6700F (trade name, JEOL Co., Ltd., Japan).

FIG. 1 shows the SEM images to illustrate the water-resistance of the nanofiber mats immediately after the electrospinning process of the electrospun solution.

In FIG. 1, in the first to fourth images in a direction from a top to a bottom, the electrospun solutions were PVA solution, PVA/PAA solution, PVA/GA solution and PVA/PAA/GA solution respectively. The "before" images shows the electron microscope images after manufacturing the nanofiber mat, and the "after" images shows the electron microscope images after treating the distilled water.

Referring to FIG. 1, it may be seen from the "before" images, that beads were not formed via the electrospinning process, and the nanofiber mats were formed using nanofibers with the constant diameter.

While, As shown in the "after" image, when treated with the distilled water, the nanofibers in the nanofiber mats as prepared with the PVA solution without the GA and PVA/PAA solution without the GA were dissolved in the distilled water. Thus, the nanofiber structure disappears, and the nanofibers change to a gel state. On the other hand, nanofibers in the nanofiber mats as prepared with the PVA/GA solution and the PVA/PAA/GA solution containing the GA were partially dissolved in the distilled water, such that the nanofiber structure is maintained to some extent. Thus, the water-resistance of the nanofiber mats as prepared with the PVA/GA solution and the PVA/PAA/GA solution containing the GA is higher than that of the nanofibers in the nanofiber mats as prepared with the PVA solution without the GA and PVA/PAA solution without the GA.

Experiment 2: Solvent Selection in Solvent Treatment Process

After the electrospinning process of the PVA/PAA solution as the electrospun solution, the nanofiber mat immediately after the electrospinning process was treated with ethanol, chloroform, dichloromethane and DMF solutions for 30 seconds and then dried. After drying the mat, the images were observed with a SEM and the results are shown in FIG. 2.

FIG. 2 shows the SEM images, each showing the nanofiber structure of the nanofiber mat after the treatment process for each solvent type.

As shown in FIG. 2, immediately after the electrospinning process using the PVA/PAA solution, the nanofiber structure with a constant diameter and no beads was confirmed as in the image corresponding to "None". However, when the nanofiber structure is treated with chloroform, ethanol and dichloromethane, the effect of melting the nanofiber appears in the solvent treatment process, which means that the diameter of the nanofiber increases and changes irregularly. On the other hand, in the treatment using DMF solution, the diameter of nanofiber is relatively maintained and the sizes of the pores formed by the nanofibers are also constant. That is, it was confirmed that the DMF may be suitably used as a solvent for increasing the crosslinking of the PVA/PAA nanofiber formed using the PVA/PAA solution.

Experiment 3: Evaluation of Water-Resistance by DMF Treatment

The nanofiber structures immediately after the electrospinning process in preparing nanofiber mats according to Present Example 1, Comparative Examples 1-a, 1-b and 2 were observed using a scanning electron microscope. Further, each of the nanofiber mats prepared according to Present Example 1, Comparative Examples 1-a, 1-b and 2 were observed using a SEM. The results are shown in FIG. 3.

Further, the nanofiber structure after treating, with distilled water, each of the nanofiber mats prepared according to Present Example 1, Comparative Examples 1-a, 1-b and 2 was observed using a SEM. The results are shown in FIG. 3.

FIG. 3 shows SEM images of the nanofiber structures after treating, with the distilled water, the nanofiber mats prepared according to Present Example 1, Comparative Examples 1-a, 1-b and 2.

In FIG. 3, "None" shows the nanofiber structures immediately after the electrospinning process; "DMF treatment" shows the nanofiber structures of the nanofiber mat finally fabricated according to the Present Examples of the present disclose, and Comparative Examples; "DMF & water treatment" shows images showing the nanofiber structures after the treatment with the distilled water. FIG. 3 shows the nanofiber mats prepared according to Comparative Example 1-b, Comparative Example 2, Comparative Example 1-a and Present Example 1 above.

Referring to FIG. 3, it may be seen that the nanofiber structure made of the electrospun solution containing the PVA had a constant diameter and was free of the beads and thus was stably produced. Further, as shown in the "DMF treatment", all of the nanofiber mats in accordance with Present Example 1, Comparative Examples 1-a, 1-b and 2 were not dissolved by the treatment with the DMF such that the diameter of the nanofibers were maintained as it was, and the sizes of the pores formed by the nanofibers were also constant.

However, it was confirmed that after the nanofiber mats prepared according to Comparative Examples 1-b and 2 were treated with the distilled water, the nanofibers thereof were dissolved in the distilled water and were gelated and thus the nanofiber structure disappeared. On the other hand, when the nanofiber mat prepared according to Present Example 1 of the present disclosure was subjected to the distilled water treatment, the nanofiber was not dissolved by the distilled water such that the nanofiber structure is maintained. The Comparative Example 1-a has water-resistance higher than that in Comparative Example 1-b or 2. The nanofiber mat manufactured according to Present Example 1 of the present disclosure further includes PAA and GA, and is subjected to the HCl vapor treatment process. Thus, the water-resistance of the mat in the Present Example 1 is remarkably better than those of the nanofiber mats prepared according to Comparative Examples 1-a, 1-b and 2.

Experiment 4: Evaluation of Water-Resistance by HCl Vapor Treatment Process and DMF Treatment Process After electrospinning process using the electrospun solution with PVA/PAA/GA solution, ① neither the HCl vapor treatment nor the DMF treatment process was performed, ② the HCl vapor treatment process was not performed and only the DMF treatment process was performed, ③ the HCl vapor treatment was performed but the DMF treatment process was not performed, and ④ both of the HCl vapor treatment and DMF treatment were performed, the resulting mats from ① to ④ were treated with the distilled water (DW) and were dried. The DW treatment results thereof were observed by the SEM. The observation results are shown in FIG. 4.

FIG. 4 shows the experimental results to illustrate the effects by the HCl vapor treatment process and the DMF treatment process.

As shown in FIG. 4, when the HCl vapor treatment was not performed (① and ②), it was confirmed that the nanofiber was completely dissolved in the distilled water and the nanofiber structure was removed. When the HCl vapor treatment was performed (③ and ④), the nanofiber structure was maintained even when the mat was treated with the distilled water. In particular, it was confirmed that even when the HCl vapor treatment is carried out in the same manner for ③ and ④, the DMF treatment (④) allows the nanofiber structure to be remarkably maintained, compared to the non-DMF treatment (③). That is, in accordance with the present disclosure, the water-resistance was significantly increased by performing the both HCl vapor treatment and DMF solution treatment.

Experiment 5: Evaluation of Optical Transparency

The nanofiber mats formed by electrospinning the PVA solution, the PVA/PAA solution, the PVA/GA solution and the PVA/PAA/GA solution were subjected to none treatment (None), to the HCl vapor treatment process (HCl vapor), to the DMF solvent treatment process (DMF), and to both the hydrochloric acid vapor treatment process and the DMF solvent treatment process (HCl vapor, DMF). Resulting samples, that is, the resulting nanofiber mats were prepared. The samples were attached to an 8-well culture plate on one face thereof. Then, the distilled water was added thereto. Then, the samples were held for 4 hours. Thereafter, transparency was evaluated by observing the visibility of characters on an opposite face of the plate. The results are shown in FIG. 5.

FIG. 5 shows photographs, each illustrating a result of transparency evaluation for each nanofiber mat.

In a bottom of FIG. 5, "+" in PVA, PAA and GA means that the corresponding component is included, while "−" means that the corresponding component is excluded. The case where the PVA is "+" and both the PAA and GA are "−" represents the nanofiber mat produced using the PVA solution; the case where both PVA and PAA are "+" and the GA is "−" represents a nanofiber mat manufactured from the PVA/PAA solution.

Referring to FIG. 5, when the PVA nanofiber mat prepared with the PVA solution subjected to the HCl vapor treatment and/or DMF solvent treatment was subjected to the treatment with distilled water, the mat becomes transparent such that the letters on the opposite face are visible. Thus, it was found that the water-resistance thereof was low and the nanofiber thereof was dissolved in the distilled water and was brought into a gel state.

When the PVA/PAA nanofiber mat prepared with PVA/PAA solution subjected to the HCl vapor treatment was subjected to the treatment with distilled water, the mat was maintained in a semi-transparent state. Thus, the water-resistance thereof was increased compared to the case where the PVA/PAA nanofiber mat was not subjected to any treatment. However, the PVA/PAA nanofiber mat prepared with PVA/PAA solution subjected to the HCl vapor treatment after the treatment with distilled water has a higher optical transparency compared to that of the PVA/GA nanofiber mat formed with PVA/GA solution or PVA/PAA/GA nanofiber mat formed with PVA/PAA/GA solution subjected to the HCl vapor treatment and/or DMF solvent treatment after the treatment with distilled water. Thus, it was confirmed that an increase in the water-resistance of the former is lower than an increase in the water-resistance of the latter.

When the PVA/GA nanofiber mat or PVA/PAA/GA nanofiber mat subjected to HCl vapor treatment and/or DMF solvent treatment was subjected to the treatment with distilled water, the mat was maintained in a semi-transparent state. Thus, the form of the PVA/GA nanofiber mat or PVA/PAA/GA nanofiber mat was not deformed by the distilled water treatment. Thus, it was seen that the water-resistance of the PVA/GA nanofiber mat or PVA/PAA/GA nanofiber mat subjected to HCl vapor treatment and/or DMF solvent treatment has very high water resistance. In this manner, the PVA/GA nanofiber mat or PVA/PAA/GA nanofiber mat subjected to the HCl vapor treatment and/or DMF solvent treatment may have a transparency and increased water-resistance.

Particularly, the mat subjected to all of the HCl vapor treatment and the DMF solvent treatment has improved water-resistance as compared to the mat subjected to either the HCl vapor treatment or the DMF solvent treatment.

Nanofiber Structure Analysis

For the PVA nanofiber mat, the PVA/PAA nanofiber mat, PVA/GA nanofiber mat and PVA/PAA/GA nanofiber mat, which were formed respectively by electrospinning the PVA solution, PVA/PAA solution, PVA/GA solution and PVA/PAA/GA solution, infrared spectroscopy results were obtained using an infrared spectrometer (Fourier-transform infrared (FT-IR, Jobin Yvon, LabRam HR Evolution-Nicolet iS50, HORIBA-Thermo Co.). The results are shown in FIG. 6.

Further, the result of the infrared spectroscopy of the PVA/PAA/GA nanofiber mat subjected to the DMF solvent treatment process on was obtained. The result is shown in FIG. 7.

FIG. 6 shows the infrared spectroscopy of the nanofiber mats before the DMF solvent treatment process. FIG. 7 shows the infrared spectroscopy of the PVA/PAA/GA nanofiber mat before and after the DMF solvent treatment.

Referring to FIG. 6, it may be seen that the PVA characteristic absorption peaks appear in the wavelength range of 3100 to 3650 $cm^{-1}$, 2800 to 2900 $cm^{-1}$, 1600 to 1750 $cm^{-1}$ and 1000 to 1100 $cm^{-1}$.

As for the peak in the 3100 to 3650 $cm^{-1}$ wavelength region (Peak I region), the PVA/PAA/GA nanofiber mat or PVA/GA nanofiber mat containing the GA and treated with the HCl vapor has a lower peak than that of the PVA nanofiber mat or PVA/PAA nanofiber mat without GA. The Peak I region is associated with stretching vibration of hydroxyl groups that have hydrogen bonds. As the crosslinking between the hydroxyl group of PVA and the CHO group of GA proceeds, the intensity of the peak decreases.

Further, as for the peak in the 1000 to 1100 $cm^{-1}$ wavelength region, which are marked as a Peak II region in FIG. 6, the peaks of the PVA/GA nanofiber mat and PVA/PAA/GA nanofiber mat containing the GA added and subjected to the HCl vapor treatment are wider than those of the PVA nanofiber mat and PVA/PAA nanofiber mat without GA. It may be seen that the increase in the area indicated by the Peak II region is due to the increase of O—C—O crosslinking resulting from the addition of the GA and from the HCl vapor treatment.

Referring to FIG. 7, when the DMF solvent treatment process is performed on the PVA/PAA/GA nanofiber mat, a peak appearing at 1650 $cm^{-1}$ in the Peak III region increase, and, at the same time, a new peak appears at 1140 $cm^{-1}$ in the Peak IV region. It may be confirmed that this peak corresponds to the peak appearing due to the increase of the crystallization of the PVA resulting from the DMF solvent treatment. The water-resistance of the nanofiber mat is increased due to the increased crystallization of the PVA resulting from the DMF solvent treatment.

Experiment 6: Cell Adhesion Assessment-1

The DMF solvent treatment process was performed on the PVA/PAA nanofiber mat, and, then, the adhesion of NIH3T3 fibroblasts or CT26 colorectal cancer cells thereto was evaluated for cell-culturing.

The fibroblasts and colon cancer cells were cultured in cell culturing devices respectively in which Dulbecco's Modified Eagle's Mediums (DMEM) contain culturing liquids containing 10% FBS 100 IU/mL penicillin and 100 µg/mL streptomycin and in which 5% $CO_2$ is maintained. The cell culturing on the nanofiber mat employed the above culturing liquids. The results are shown in FIG. 8.

FIG. 8 shows photographs for illustrating the cell adhesion evaluation results for the nanofiber mat prepared according to Comparative Example 2. As shown in FIG. 8, the cells did not adhere to the surface of the nanofiber, and cell clumping between the cells occurred until the cells were incubated for 3 days. Namely, as for the nanofiber mat prepared according to Comparative Example 2, the water-resistance may be improved to some extent by DMF solvent treatment thereof, but the cell attachment ability thereto is very poor and thus the mat cannot be used as a cell-culturing nanofiber mat.

Experiment 7: Cell Adhesion Assessment-2

As for the nanofiber mat manufactured according to Present Example 1 of the present disclosure, in order to attach two different cells to the nanofiber mat on both faces of the nanofiber mat, a filter of the Corning Costa transwell assay chamber was removed and the nanofiber mat was attached thereto.

FIG. 9 is a view for illustrating a process for fabricating a cell-culturing nanofiber mat using a nanofiber mat manufactured according to Present Example 1 of the present disclosure. In order to attach CT26 colon cancer cells to a bottom layer of the nanofiber mat attached to the chamber as shown in FIG. 9, the chamber was upside down, and 5×10$^4$ cells stained with PKH26 red fluorescence were placed on the bottom face of the nanofiber mat and then were cultured for 4 hours. Onto the top face of the nanofiber mat, 5×10$^4$ NIH3T3 fibroblasts green fluorescent stained with PKH67 were attached. The cells attached to the top and bottom layers were observed from above using an up-light microscope (Nikon, Japan), and were observed from below using an inverted microscope, which is a confocal fluorescence microscope (K1 confocal microscope, Nanoscope System Co., Daejeon, Korea). The results are shown in FIGS. 10 to 13.

FIGS. 10 to 13 show photographs for illustrating the cell adhesion evaluation results for the nanofiber mat manufactured according to the process of FIG. 9.

FIG. 10 shows the result of measurement on the top face with an optical microscope. As shown in FIG. 10, it may be seen that when the cancer cells and fibroblasts were adhered to both faces of the nanofiber mat, the 2 types of cells are observed simultaneously using the optical microscope. The fibroblasts exhibited some cell aggregation, but the cancer cells were well attached as shown by the arrow in FIG. 10.

FIG. 11 shows the result of the measurement on the bottom face with fluorescence microscopy. As shown in FIG. 11, the confocal microscopy observed that the 2 types of cells were stained with different fluorescence colors and were present on the bottom of the nanofiber mat at the same time.

FIG. 12 shows the confocal microscope observation and then Z-stack analysis result for different types of cells attached to the top/bottom layers of the nanofiber mat which in turn were cultured for 24 hours. Referring FIG. 12, the 2 types of cells were observed at the same time and these cells were found to overlap.

FIG. 13 shows the observation of the attachment or non-attachment of the cells to the nanofiber mat via an electron microscope. As shown in FIG. 13, the cells attached to both faces and the nanofiber sample were fixed for electron microscopic observation. When observing each cell on each face, the cancer cells and fibroblasts were attached thereto.

The descriptions of the presented embodiments are provided so that one of ordinary skill in the art of the present disclosure may use or implement the present disclosure. Various modifications to these embodiments will be readily apparent to those skilled in the art of the present disclosure. The generic principles defined herein may be applied to other embodiments without departing from the scope of the present disclosure. Thus, the present disclosure is not to be limited to the embodiments set forth herein but is to be accorded the widest scope consistent with the principles and novel features presented herein.

What is claimed is:

1. A method for producing a cell-culturing polyvinyl alcohol-based nanofiber structure, the method comprising:
   electrospinning an electrospun solution to form a nanofiber mat, wherein the electrospun solution contains polyvinyl alcohol (PVA), polyacrylic acid (PAA) and glutaraldehyde (GA);
   crosslinking the nanofiber mat via a hydrochloric acid (HCl) vapor treatment; and
   treating the crosslinked nanofiber mat with dimethylformamide (DMF) solvent to crystallize the nanofiber mat.

2. The method according to claim 1, wherein forming the nanofiber mat comprises:
   electrospinning the electrospun solution at a spinning rate of 5 to 10 μl/min using a metal syringe at 10 to 15 kV to form nanofibers; and
   performing a thermal treatment of the nanofibers.

3. The method according to claim 1, wherein crosslinking the nanofiber mat comprises:
   adding the nanofiber mat and hydrochloric acid (HCl) into a vacuum desiccator and treating the nanofiber mat with the HCl vapor under vacuum for 60 to 120 seconds.

4. The method according to claim 1, wherein crystallizing the nanofiber mat comprises:
   treating the crosslinked nanofiber mat with the dimethylformamide (DMF) solvent for 20 seconds to 1 minute; and
   drying the nanofiber mat.

5. The method according to claim 1, wherein the crystallized nanofiber mat via the crystallizing is not gelated when the crystallized nanofiber mat is treated with distilled water.

6. The method according to claim 1, wherein the method further comprises: after the crystallization, adhering two or more different kinds of cells on both faces of the crystallized nanofiber mat respectively, culturing the cells, and observing the cells on the both faces at the same time.

* * * * *